United States Patent [19]

Liljewall

[11] Patent Number: 5,087,424
[45] Date of Patent: Feb. 11, 1992

[54] APPARATUS FOR MECHANICAL PROCESSING OF A SAMPLE AND A MEMBER OF SUCH AN APPARATUS

[75] Inventor: Lars R. Liljewall, Ödåkra, Sweden

[73] Assignees: Kabi Pharmacia AB, Uppsala; Akstiebolaget Leo., Helsingborg, both of Sweden

[21] Appl. No.: 382,629
[22] PCT Filed: Dec. 12, 1988
[86] PCT No.: PCT/SE88/00674
§ 371 Date: Aug. 1, 1989
§ 102(e) Date: Aug. 1, 1989
[87] PCT Pub. No.: WO89/05970
PCT Pub. Date: Jun. 29, 1989

[30] Foreign Application Priority Data

Dec. 14, 1987 [SE] Sweden .................. 8704963

[51] Int. Cl.⁵ ............................. G01N 1/10
[52] U.S. Cl. ................. 422/68.1; 100/37; 264/344; 425/398; 436/174; 436/177
[58] Field of Search ........... 436/174, 177; 422/68.1; 261/36.1, 122; 264/344, 232, 349; 425/398; 100/37, 291

[56] References Cited

U.S. PATENT DOCUMENTS

| | | | |
|---|---|---|---|
| 3,552,928 | 1/1971 | Fetter | 436/177 X |
| 3,625,834 | 12/1971 | Muller et al. | 261/36.1 |
| 4,127,378 | 11/1978 | Meadors | 425/398 |
| 4,767,602 | 8/1988 | Johnson | 436/177 X |

FOREIGN PATENT DOCUMENTS

| | | |
|---|---|---|
| 0142574 | 5/1985 | European Pat. Off. |
| 943567 | 7/1982 | U.S.S.R. ............... 422/68.1 |
| 2136123 | 9/1984 | United Kingdom. |

OTHER PUBLICATIONS

Journal of Dental Research "A Mastication Device Designed for the Evaluation of Chewing Gums", C. J. Kleber et al. (1981):2, pp. 109–114.
Arch. Pharm. Chem., Sci. Ed. 1986, 14, 30–36 "Chewing Gum as a Drug Delivery System", Lona L. Christrup et al., 9 Sep. 1985.

Primary Examiner—Richard L. Chiesa
Attorney, Agent, or Firm—Fred Philpitt

[57] ABSTRACT

An apparatus for facilitating the release of an ingredient of a plastic or elastic sample of a pharmaceutical or confectionery material while the sample is in contact with a liquid medium which includes a base, a fixed lower jaw, a movable upper jaw and a member for moving the upper jaw toward and away from the lower jaw, a support for mounting and supporting a sample in the space between the upper surface of the lower jaw and the lower surface of the upper jaw, and a container surrounding both the jaws and sample so as to confine a liquid medium to the area surrounding the sample.

5 Claims, 2 Drawing Sheets

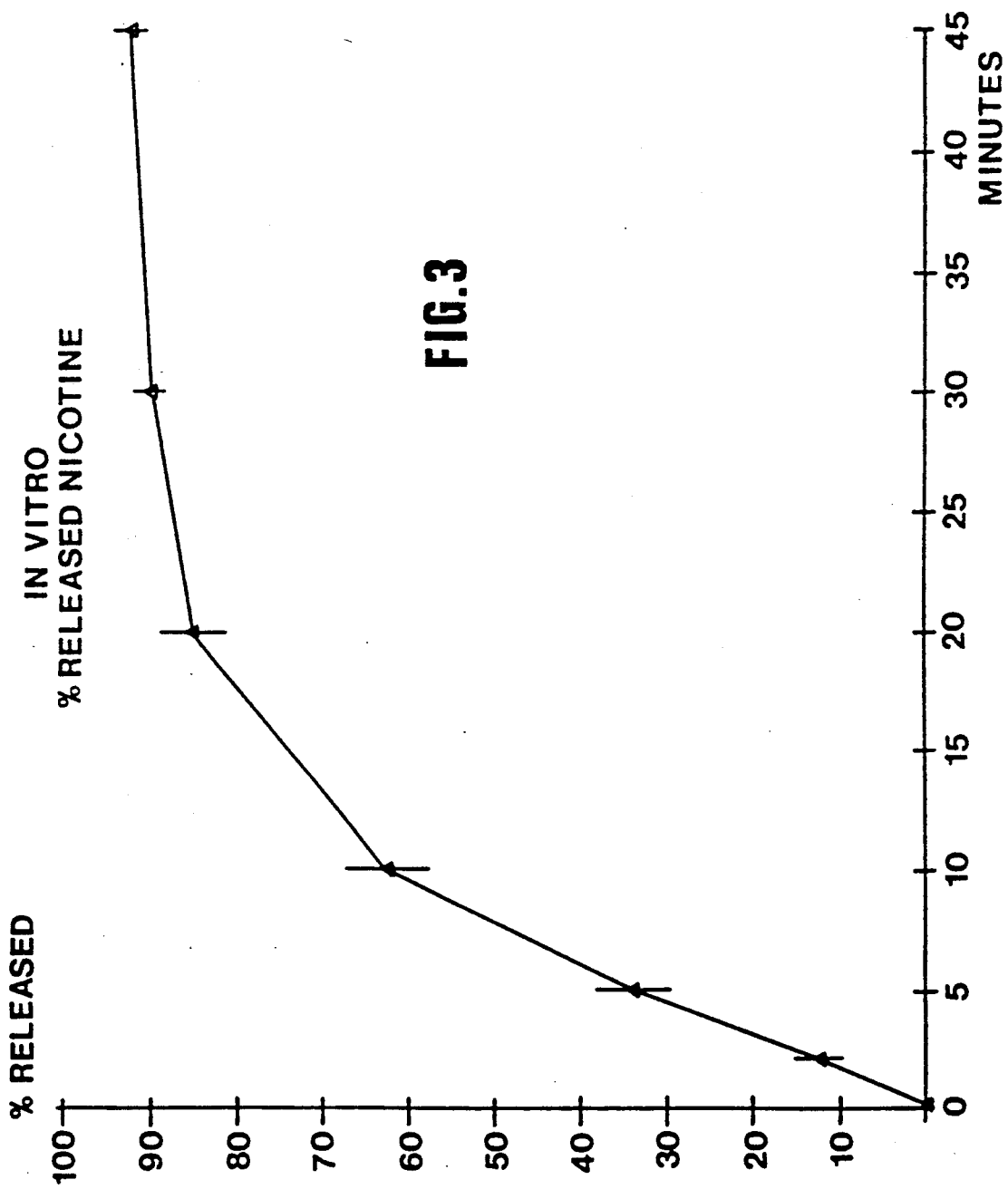

APPARATUS FOR MECHANICAL PROCESSING OF A SAMPLE AND A MEMBER OF SUCH AN APPARATUS

The present invention relates to a method and an apparatus for mechanical processing of a plastic or elastic sample and to a member of such an apparatus.

BACKGROUND

For studying the properties of a plastic or elastic sample when subjected to mechanical processing, an apparatus is needed which makes it possible to carry out reproducible tests.

Present-day techniques comprise e.g. a masticating device as disclosed by Kleber et al. in Journal of Dental Research, 60 (1981):2, pp 109-114, which is used for in vitro assessment of the abrasive effects of chewing gum on teeth, and a measuring device as described by Christrup et al. in Arch. Pharm. Chem. Sci., 1986, 14, pp 30-36, which is used for in vitro measurements of the release of substances included in a chewing gum.

The prior art devices comprise two mutually reciprocatory jaws or pistons which are disposed in a container and between which the sample is to be processed.

The properties which may be of interest to determine thus are, inter alia, the action exerted by the sample on the pistons or some part thereof, the plasticity of the sample and/or the release of substances included in the sample to a liquid surrounding it, all as a function of the processing time and/or the processing technique. The purpose of the determination may be comparative, i.e. primarily for quality control, and/or imitative, e.g. with respect to in vivo processing by chewing.

A particularly interesting field for using such a mechanical processing apparatus is the processing of pharmaceutical preparations in the form of plastic samples, preferably chewing gums, in which case it should be possible in a reproducible manner to determine the period of time during which active substances in the sample are released to a liquid surrounding the sample.

In addition to the processing technique, the release of substances may be affected by the components included in the chewing gum, such as consistency agents, softeners, preservatives, gum bases, flavourings, as well as active substances in the form of drugs or nicotine, but also by the method of making the chewing gum. Further, the release is affected by the environment in which it takes place, i.e. the temperature and the composition of the liquid surrounding the sample, and the apparatus should be able to maintain at least the temperature constant.

One drawback of the prior art devices is the problem of cleaning the container or reservoir in which the sample is processed. The tendency of the sample to move or spread outside the processing area of the pistons or jaws has also been observed in the prior art devices. Another problem concerns the fact that the sample tends to adhere sometimes to one jaw, sometimes to the other and, above all, to separate parts floating freely in the liquid and escaping further processing.

In view of these problems, it is therefore very difficult to obtain an exact and reproducible processing of the samples by using the prior art devices. From this of course follows that it will not be possible to obtain reliable and reproducible release rates which can be used for scientific or manufacturing purposes.

THE PRESENT INVENTION

The most important object of the present invention thus is to provide an apparatus and a method for mechanical processing of a pharmaceutical or confectionery sample in a reproducible manner.

To sum up, the present invention concerns an apparatus for mechanical processing of a pharmaceutical or confectionery plastic or elastic sample for the release of substances from the sample into a surrounding liquid medium. The apparatus includes a substantially vertical container releasably mounted on a base. The apparatus also comprises a first jaw for receiving the sample. This jaw is fixed to the base and arranged in the lower end of the container. Means for sealing the lower end of the container against leakage of the liquid are also provided. A second jaw facing the first jaw is vertically movable and rotatable for subjecting the sample to compression and shearing forces. The apparatus also includes means for driving the second jaw.

Preferably, the apparatus also includes means for controlling the temperature of the liquid medium.

According to the invention, it has also been found that in cases where a high degree of accuracy and reproducibility is required, a separate reinforcing member which may be in the form of a flat and/or disc-shaped device or member should be processed at the same time as the sample. By using this disc-shaped device or reinforcing member the sample will hold together and can be prevented from splitting up into several pieces or from otherwise moving outside the processing area between the jaws.

To permit a substantially free movement within the material of the sample during processing, the disc-shaped member suitably is foraminated. This also increases the adherence between the member and the sample, making it more vigorous than the adherence between the sample and the jaws.

The disc-shaped member may advantageously be a net or a perforated disc and consist of plastic, e.g. nylon or any other material which is inert to the components in the sample and to the liquid in which the sample is processed.

It is furthermore preferred that the container is double-walled and made of a transparent material, such as glass or plastic. The flexibility of the apparatus is further increased if the distance between the jaws can be adjusted and, to this end, the upper jaw is preferably mounted in such a way that it is vertically adjustable.

The surfaces of the jaws facing each other suitably are friction surfaces, i.e. exhibit a relatively large friction with respect to the sample. A particularly suitable feature is however using smooth friction surfaces, in which case the necessary friction may optionally be achieved by blasting. Completely smooth surfaces may however also be used. In such case, the jaws will be very easy to clean, which is of importance to prevent a sample from contaminating the following sample and so forth.

In order to ensure stirring of the liquid in the container during processing, at least one jaw suitably forms a gap with the inner wall of the container.

The movement of the upper jaw may be purely reciprocating, but in order to imitate in vivo processing of a chewing gum, the apparatus may preferably have means for rotating the jaws relative to each other when in their turning positions closest to each other.

The invention also comprises a method for mechanical processing of a plastic or elastic pharmaceutical or confectionery sample for the release of substances from the sample into a surrounding liquid medium, comprising immersing a reinforcing member in the medium, immersing the sample in the medium, and subjecting the sample and the member essentially simultaneously to repeated compression and shearing forces.

BRIEF DESCRIPTION OF THE DRAWINGS

Preferred embodiments of the invention will now be described in more detail hereinbelow with reference to the accompanying drawing in which:

FIG. 3 is a diagram showing release of nicotine versus time.

DETAILED DESCRIPTION OF THE PREFERRED EMBODIMENTS

Figure 1:
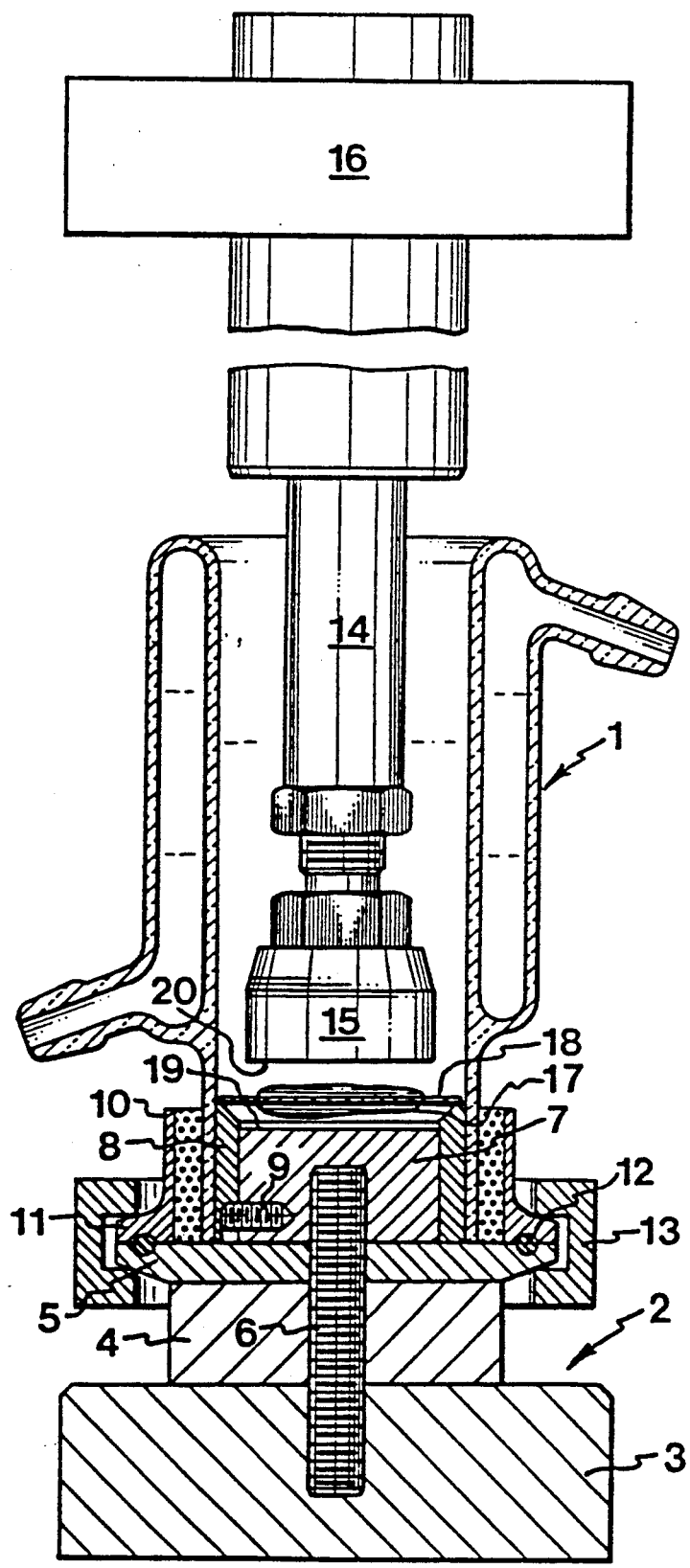
FIG. 1 is a longitudinal section of an apparatus according to the invention.

The embodiment shown in FIG. 1 of an apparatus according to the invention comprises a cylindrical, double-walled container 1. A base 2 consists of a base plate 3, a spacer plate 4 and a sealing plate 5 which are held together by a stud bolt 6 on which a fixed jaw 7 can also be screwed. A spacer sleeve 8 encloses the jaw 7 and is removably mounted and non-rotatably connected to the jaw 7 by means of a stop screw 9.

The lower open end of the container 1 can be passed over the sleeve 8 with liquid-tight fit with respect thereto. A collar 10 with a flange 11 is glued to the lower end of the container 1. An O-ring 12 is mounted in mating grooves in the flange 11 and the sealing plate 5 which are pressed against each other by means of a clamping member 13.

A second jaw 15 is removably mounted on a reciprocatory piston 14, such that the jaw 15 is located above the jaw 7. The jaw 15 can be reciprocated relative to the jaw 7 by drive means (indicated at 16) and has adjustable stroke length, stroke velocity and stroke frequency. The drive means 16 can also be arranged to rotate the jaw 15 relative to the jaw 7, especially when the jaw 15 is in its turning position closest to the jaw 7.

Figure 2:
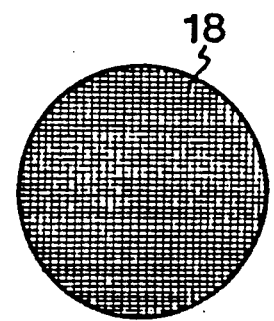
FIG. 2 is a top plan view of a device according to the invention.

In FIG. 1, there is also shown a sample 17 which partly encloses a disc-shaped member 18 according to the invention. The disc-shaped member 18 more specifically is in the form of a net, as shown in more detail in FIG. 2, and is circular, having a slightly smaller diameter than the inner diameter of the container 1, for instance 1 mm less. The net 18 has a higher adhesive capacity with respect to the sample 17 than the jaws 7, 15.

Instead of a net, the disc-shaped member 18 may consist of any other foraminated member, for instance a perforated disc. The member 18 should be substantially two-dimensional, i.e. have but a small extent in the direction of movement of the jaw 15. Alternatively, the member 18 could however also be a spacer element determining the minimum distance between the jaws 7 and 15, i.e. the lower end position of the jaw 15.

Since the container 1 is double-walled, it can be used for thermostatting a liquid contained therein, such as water or artificial saliva. The container may consist of glass, plastic or other suitable material that does not react with the liquid used or any of the components in the sample 17.

The surfaces 19, 20 of the jaws 7, 15 facing each other are friction surfaces which may be formed with grooves, notches or other irregularities to retain the sample 17 when it is subjected to pressure and rotation by the jaws 7, 15. However, the required friction can also be achieved by means of smooth surfaces, which of course makes it easier to clean the jaws 7, 15 between different processing operations.

It is desirable to have a gap between the jaw 15 and the inner wall of the container 1. The size of this gap is suitably determined empirically on the basis of e.g. the desired stroke frequency, the volume of the sample and the liquid volume to be displaced. Since it is often desirable to have liquid solutions with as high a concentration as possible of substances released from the sample during the processing, the liquid volume in the container should be relatively small and thus also said gap.

For analysing substances released from the sample 17, the apparatus may comprise different types of probes for measuring pH and temperature, and for automatic measurements of the composition of the liquid etc.

To determine e.g. the release of different substances in a sample 17, the apparatus described above can be used in the following way. The sample 17 and the member 18 are placed on the jaw 7, whereupon a suitable liquid is supplied to and thermostatted in the container 1. The jaw 15 is thereafter set in motion according to a predetermined movement pattern, and sampling from the liquid container 1 is performed at preselected points of time, whereupon the sample or liquid phase is analysed with respect to the substance or substances the release of which should be measured.

During processing, the plastic sample 17 will be flattened and partly enclose the member 18 thus performing a reinforcing function and holding the sample 17 together. If, nevertheless, parts of the sample 17 should be torn loose from the side thereof located below the member 18, this will prevent the separated parts from moving upwards into the liquid. In this way, the separated parts can again be easily integrated with the sample reinforced by the member 18. Since the spacer sleeve 8 extends higher than the jaw 7, the member 18 tends to lift the sample 17 off the jaw 7 between each stroke of the jaw 15.

EXAMPLES

The invention is further illustrated by the following Examples

EXAMPLE 1

Samples of NICORETTE chewing gum were weighed.

The casing of a double-walled container in an apparatus according to the invention was filled with water to be circulated and having a temperature of 37° C. An aqueous solution containing 0.1% artificial saliva was heated to 37° C. and poured in the container. A sample of NICORETTE was immersed into the aqueous medium in the container and placed on the jaw. The upper jaw was actuated to move to a depressed position for fixing the sample. After about 5 min, temperature equilibrium between medium and sample had been reached, and the upper jaw was actuated to move up and down, executing a rotary movement when in its lowest turning position in order to repeatedly subject the sample to compression and shearing forces.

EXAMPLE 2

Example 1 was repeated, however with a disc-shaped net immersed into the medium in the container together with the NICORETTE sample. Volumes of 0.5 ml of the medium were withdrawn from the container after respectively 2, 5, 10, 20, 30 and 45 min, and the amount of nicotine in each volume was analysed by standard methods. The results (mean values of 6 samples) are given in the diagram of FIG. 3.

It is evident to a person skilled in the art that several different modifications of the embodiments described above are possible within the scope of the invention, such as it is defined in the accompanying claims.

I claim:

1. An apparatus for facilitating the release of an ingredient of a plastic or elastic sample of a pharmaceutical or confectionery material while the sample is in contact with a liquid medium, said apparatus comprising the combination of
   (a) a base (2),
   (b) a first jaw (7) fixed on said base (2) and having an upper surface (19) against which a sample positioned immediately thereabove can be compressed,
   (c) a second jaw (15) positioned above said first jaw and having a lower surface against which said sample positioned immediately therebelow can be compressed,
   (d) support means (8) for supporting a sample at a point which is intermediate the upper surface of said first jaw (7) and the lower surface of said second jaw (15), said support means including a separate member (18) that is foraminated so that a sample will extend above, below and through the separate member (18),
   (e) means (14, 16) for moving said second jaw (15) toward and away from said first jaw (7) and which is capable of imparting a rotary movement to said second jaw when said jaw is in its lowest position so that said jaws will repetitively knead a sample placed therebetween; and
   (f) a vertical container (1) extending upwardly from said base (2) and closely surrounding said first and second jaws (7, 15) so as to confine a liquid medium to the area surrounding said sample.

2. Apparatus according to claim 1 wherein said container (1) is a cylinder.

3. Apparatus according to claim 2 wherein the cylinder (1) is double-walled and made of a transparent material.

4. Apparatus according to claim 3 wherein said transparent material is glass.

5. An apparatus according to claim 1 wherein said separate member (18) is a net which is inert to the sample and to the liquid medium.

* * * * *